United States Patent [19]

Bombardelli et al.

[11] Patent Number: 4,709,076

[45] Date of Patent: Nov. 24, 1987

[54] METHODS, COMPOSITIONS AND COMPOUNDS FOR THE TREATMENT OF PROSTATIC ADENOMA

[75] Inventors: Ezio Bombardelli; Bruno Gabetta; Marisa Conti, all of Milan, Italy

[73] Assignee: Inverni Della Beffa SpA, Milan, Italy

[21] Appl. No.: 743,073

[22] Filed: Jun. 10, 1985

[30] Foreign Application Priority Data

Jun. 11, 1984 [IT] Italy .................................. 21342 A/84

[51] Int. Cl.$^4$ ............................................. C07C 69/76
[52] U.S. Cl. ....................................... 560/55; 514/532; 560/104
[58] Field of Search .................... 560/55, 104; 514/532

[56] References Cited

PUBLICATIONS

Komatsu, M. Chem. Pharm. Bull. 26 (12) 3863-70, 1978.
Adamovics, J. A., Phytochemistry (16)7 1089-90, 1977.
Kumari, D. et al., Indian J. Chem. Sect. B 17B(2) 181-2, 1979.

Primary Examiner—Paul J. Killos
Attorney, Agent, or Firm—Browdy and Neimark

[57] ABSTRACT

Unsaturated esters of formula I

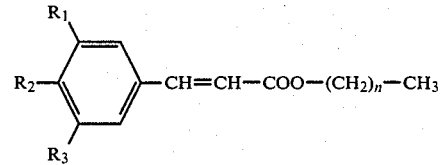

in which $R_1$, $R_2$ and $R_3$, which are the same or different to one another, represent hydrogen, hydroxyl, methoxyl or acetoxyl; n is between 13 and 25; are useful in the treatment of prostatic hyperplasia or hypertrophy.

14 Claims, No Drawings

METHODS, COMPOSITIONS AND COMPOUNDS FOR THE TREATMENT OF PROSTATIC ADENOMA

The present invention relates to methods of treating disorders connected with prostatic hyperplasia, to pharmaceutical compositions for use in such methods and to novel esters of trimethoxycinnamic acid and isoferulic acid.

Prostatic hyperplasia, with consequent obstruction of the urethra, is a very common medical condition in males during the ageing period and, although not being a cause of death when benign, is the major source of pathological conditions of the urogenital system in old age.

Although many aetiological aspects still need to be clarified, enlargement of the prostate is certainly linked with a change in the metabolism of the testicular hormones which gradually establishes itself with age. In recent years, a considerable mass of data has emerged concerning endocrine control of prostate growth, the effect of age on hormone dynamics in males and changes in the mediators at the level of the target organ.

United Kingdom Patent Specification No. 1 459 233 describes pharmaceutical compositions based on higher alkanols for the treatment of prostatic adenoma, and mentions in a general manner the possible esters of the said alkanols. However the specification gives no specific examples of or any data on the biological activity of the esters.

The present invention is based on the finding that a specific class of esters, as defined by formula I below, is endowed with particularly advantageous biological characteristics.

Thus according to the present invention there is provided a method for the prophylaxis or treatment of prostatic hypertrophy or hyperplasia in a male subject which comprises administering an effective dose of at least one compound of formula

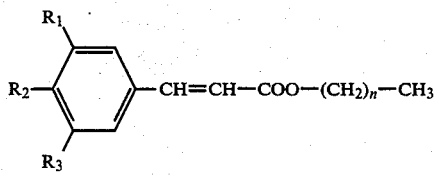

in which $R_1$, $R_2$ and $R_3$ which may be the same or different are selected from hydrogen, hydroxyl, methoxyl or acetoxyl, and n is from 13 to 25.

The invention also relates to the use of compounds of Formula I for the prophylaxis or treatment of prostatic adenoma, hypertrophy or hyperplasia including medical and/or veterinary use and industrial use in the manufacture of products for medical and/or veterinary administration.

The invention thus further provides pharmaceutical or veterinary compositions for the prophylaxis or treatment of prostatic hypertrophy or hyperplasia comprising as active ingredient a compound of formula

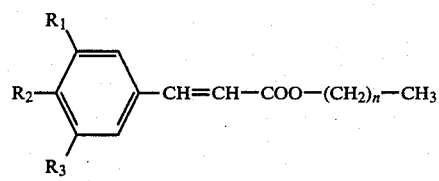

in which $R_1$, $R_2$ and $R_3$, which may be the same or different are selected from hydrogen, hydroxyl, methoxyl or acetoxyl and n is from 13 to 25, and a pharmaceutically acceptable carrier.

Certain compounds useful in carrying out the method of the invention, specifically esters of isoferulic acid (i.e. compounds of Formula I in which $R_1$=H, $R_2$=OCH$_3$, $R_3$=OH) and esters of 3,4,5-trimethoxycinnamic acid (i.e. compounds of Formula I in which $R_1$=$R_2$=$R_3$=OCH$_3$) are novel and constitute a further aspect of the present invention.

The compounds of Formula I are believed to intervene biologically in the alteration of a number of hormonal parameters of the hypophysis-suprarenal-gonadal system which may have been impaired by pathological conditions, with a consequent improvement in prostatic functionality. It has been found, in fact, that the said compounds induce in test animals reductions in prolactinaemia, in luteinizing hormone and in the plasmatic levels of testosterone and correlated steroids. The reduction in prolactinaemia, a notoriously important factor in the improvement of the dependent prostatic gonad function has proved to be of particular interest. Moreover, regarding the functional aspect of the prostate, it has been possible to show favourable results connected with androgen turnover by means of suitable pharmacological tests.

In test animals, after prolonged treatment with compounds of Formula I, it has been possible to verify that (1) on treating rats as soon as they have been weaned and castrated or adrenalectomized, the compounds of Formula I increase the metabolism of androgens in target organs such as the thymus and the prostate, compared to controls, and (2) on treating older rats (age more than 1 year), again with the same substances, an improvement in glandular activity can be shown.

The esters according to the present invention may be prepared according to classical methods from a carboxylic acid derivatives of Formula II

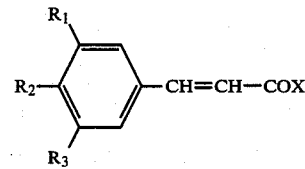

in which $R_1$, $R_2$ and $R_3$ are as defined above, with the proviso that any hydroxyl groups are suitably protected, and X represents an electron withdrawing group, for example a halogen atom by reaction with an alkanol of formula CH$_3$—(CH$_2$)$_n$—CH$_2$OH where n is as defined above.

Alternatively, the compounds I may be prepared from suitable carboxylic acid salts of Formula IIa

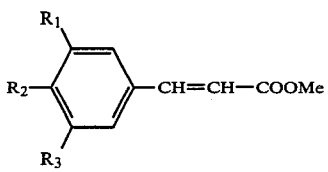

where Me represents a cation, for example, a cation of an alkali metal or alkaline earth metal and $R_1$, $R_2$ and $R_3$ are as defined above, by reaction with a compound of formula $CH_3(CH_2)_nY$, wherein Y is a leaving group, for example a halogen atom or an alkyl or arylsulphonyl group, as for example in an alkyl halide or an arylsulphonic ester of the above alkanol.

Examples of particularly preferred alkanols are 1-docosanol, 1-eicosanol and 1-tetracosanol, while the preferred acids are ferulic, isoferulic, caffeic and 3,4,5-trimethoxycinnamic acid.

The following Examples further illustrate the invention, without constituting a limitation thereof.

EXAMPLE 1

Docosyl 3-methoxy-4-hydroxycinnamate 3.26 g of n-docosanol are dissolved in 50 ml of pyridine in a multi-necked 100 ml flask equipped with a stirrer, a thermometer and a dehydrating valve, while heating gently to 40° C. To this solution there are added under agitation 3.05 g of 4-acetoxy-3-methoxycinnamoyl chloride. After about one hour, crystallization of docosyl 4-acetoxy-3-methoxycinnamate begins, which is filtered and repeatedly washed with water so as to eliminate the pyridine. The product obtained in this way is dried under vacuum over night at 50° C. 6.4 g of dry product are obtained which are dissolved in 30 ml of a mixture of benzene and piperidine in a ratio of 1:1 and left to stand for 24 hours. Under these conditions, complete deacetylation of the docosyl 4-acetoxy-3-methoxycinnamate occurs. The solution is concentrated at low temperature under vacuum to a small volume. The oily residue is poured into a dilute solution of aqueous hydrochloric acid in the presence of ethyl acetate.

The organic phase, rendered anhydrous over $Na_2SO_4$, is concentrated to dryness under vacuum. The residue is taken up in 20 ml of acetonitrile. 4.2 g of docosyl 4-hydroxy-3-methoxycinnamate crystallize out and, after drying over night at 60° C., is found to have the following characteristics:

| M.p. 74° C. | $M^+$ 502 | |
|---|---|---|
| Analysis for $C_{32}H_{54}O_5$ | Found C % 76.51 | H % 10.72 |
| | Calculated C % 76.49 | H % 10.75 |

EXAMPLE 2

Docosyl 3-hydroxy-4-methoxycinnamate 60 ml of anhydrous pyridine and 6.52 g of n-docosanol are dissolved in a multi-necked 100 ml flask equipped with a stirrer, a thermometer and a dehydrating valve. 3.44 g of p-toluene sulphonylchloride are added to the solution in small portions. After standing over night, the reaction mixture is poured over 100 g of ice, an abundant precipitate being obtained which is filtered. After careful washing with water, the solid is dried over night under vacuum at 60° C.

8.5 g of docosyl p-toluenesulphonate are obtained which are dissolved in 100 ml of anhydrous dimethylformamide. To this solution there are added, under brisk agitation and at a temperature of 50° C., 50 ml of a solution of dimethylformamide containing 4.5 g of the sodium salt of 3-hydroxy-4-methoxycinnamic acid.

The reaction mixture is agitated for 8 hours, the temperature being maintained at 50° C., and then it is cooled and poured into 500 ml of water.

6.2 g of docosyl 3-hydroxy-4-methoxycinnamate having the following characteristics are precipitated:

| M.p. 72° C. | $M^+$ 502 | |
|---|---|---|
| Analysis for $C_{32}H_{54}O_4$ | Calculated C % 76.49 | H % 10.75 |
| | Found C % 76.51 | H % 10.78 |

EXAMPLE 3

Docosyl 3,4,5-trimethoxycinnamate 3.26 g of 1-docosanol dissolved in 50 ml of anhydrous pyridine are placed in a 100 ml flask equipped with a stirrer, a thermometer and a dehydrating valve. To this solution there are added 2.5 g of trimethoxycinnamoyl chloride and 0.01 ml of $POCl_3$. The reaction mixture is left at room temperature over night and is then poured into 200 ml of water.

After filtration, the precipitate formed is crystallized from 30 ml of isopropanol. After drying, there are obtained 4.6 g of docosyl trimethoxycinnamate having the following characteristics:

| M.p. 70–72° C. | $M^+$ 546 | |
|---|---|---|
| Analysis for $C_{34}H_{58}O_5$ | Calculated C % 74.72 | H % 10.62 |
| | Found C % 74.70 | H % 10.58 |

EXAMPLE 4

Docosyl Caffeate 3.26 g of docosanol dissolved in 50 ml of anhydrous pyridine are placed in a 100 ml flask equipped with a stirrer, a thermometer and a dehydrating valve. To this solution there are added 3.2 g of 3,4-diacetoxycinnamoyl chloride and the reaction mixture is agitated at room temperature for 12 hours. The reaction mixture is poured into 300 ml of ice water and left in a refrigerator over night. The precipitated solid is filtered and, after careful washing with water, is dried under vacuum at room temperature in the presence of $P_2O_5$.

The dried product is taken up in 30 ml of a 1:1 benzene/piperidine mixture and kept at 30° C. for 10 hours. The reaction mixture is poured into 300 ml of water. After acidification with hydrochloric acid to pH 3, the product is extracted with 200 ml of ethyl acetate.

The organic phase is dehydrated over anhydrous sodium sulphate and is concentrated to dryness. The residue obtained is taken up in 20 ml of a 1:1 ethyl acetate/benzene mixture and chromatographed, eluting with the same mixture on 40 g of silica gel.

The fractions containing the product are combined, concentrated to dryness under vacuum and crystallized from acetonitrile.

3.2 g of docosyl caffeate having the following characteristics are obtained:

| M.p. 105–107° C. | $M^+$ 488 |
|---|---|

| Analysis for $C_{31}H_{52}O_4$ | Calculated C % 76.22 | H % 10.65 |
|---|---|---|
| | Found C % 76.12 | H % 10.61 |

EXAMPLE 5

Eicosyl 3,4,5-trimethoxycinnamate 2.9 g of 1-eicosanol dissolved in 50 ml of anhydrous pyridine are placed in a 100 ml flask equipped with a stirrer, a thermometer and a dehydrating valve. To this solution there are added 2.5 g of trimethoxycinnamoyl chloride and 0.01 ml of $POCl_3$. The reaction mixture is left alone at room temperature overnight and is then poured into 200 ml of water. After filtration, the precipitate formed is crystallized from 30 ml of methanol. After drying, 4.2 g of eicosyl trimethoxycinnamate having the following characteristics are obtained:

| M.p. 82° C. | $M^+$ 518 | |
|---|---|---|
| Analysis for $C_{32}H_{54}O_5$ | Calculated C % 74.13 | H % 10.42 |
| | Found C % 74.11 | H % 10.41 |

EXAMPLE 6

Tetracosyl 3-methoxy-4-hydroxycinnamate 3.54 g of tetracosanol are dissolved in a multi-necked 100 ml flask equipped with a stirrer, a thermometer and a dehydrating valve in 30 ml of anhydrous pyridine while heating gently to 40° C. When dissolution is complete, 3.05 g of 4-acetoxy-3-methoxycinnamoyl chloride are added with agitation.

After about one hour, crystallization of tetracosyl 4-acetoxy-3-methoxycinnamate from the pyridine begins and, after standing over night at room temperature, the reaction mixture is filtered and the solid obtained is carefully washed and dried. The product obtained in this way is treated with 30 ml of a mixture of piperidine and benzol at a temperature of 40° C. for 2 hours. After concentration of the solvent and elimination of the piperidine with hydrochloric acid, tetracosyl 4-hydroxy-3-methoxycinnamate is obtained, which is recrystallized from acetonitrile.

The compound obtained has the following characteristics:

| M.p. 82-84 | $M^+$ 530 | |
|---|---|---|
| Analysis for $C_{34}H_{58}O_4$ | Calculated C % 76.98 | H % 10.94 |
| | Found C % 77.00 | H % 10.96 |

PHARMACOLOGICAL DATA

The prostatotrophic, antiprolactinic and antitestosteronic activities of the compound of Example 1 were evaluated as follows:

A. Determination of Prostatotrophic Activity

Groups of 20 6-month old male Wistar rats, castrated at least 15 days before randomization and carefully weighed, were treated daily with 2.5-5-10 mg/kg of docosyl 3-methoxy-4-hydroxycinnamate for one month by oral administration, and the rats then were killed by decapitation. Immediately after sacrifice, the prostate, seminal vesicles and suprarenal glands were removed and weighed. There was a statistically significant increase in the weight of the prostate and the suprarenal gland with respect to the controls. Both from weight and from histological examination it was apparent that there was an increased prostatic functionality due to an increased production of non-testicular androgens on the part of the suprarenal gland.

B. Determination of Antiprolactinic and Antitestosteronic Activity

Groups of 20 18-month old male Wistar rats were treated for 45 days by probe with 2.5-5-10 mg/kg of docosyl 3-methoxy-4-hydroxycinnamate dissolved in 0.1 ml of arachis oil. At the end of the treatment, the haematic concentrations of prolactin and testosterone were measured by radioimmunological methods.

The prolactin levels were reduced by 38% (P 0.05) at a dose of 5 mg/kg and by 45% at 10 mg/kg and the plasma testosterone levels were found to be reduced respectively by 20% at 5 mg/kg and 32% at 10 mg/kg.

Histological examination of the prostates of the animals after sacrifice showed signs of increase in secretory activity with respect to the controls.

In male animals, for example human males, the compounds of the present invention may be used to reduce functional disorders of the prostate such as diurnal and nocturnal pollakiuria and dysuria in a short time and have a decongestive effect on the organ in cases of bacterial prostatitis and in prostatodynia.

The pharmaceutical compositions to which the present invention relates, as indicated, may contain at least one of the compound of Formula I in admixture with acceptable pharmaceutical diluents or carriers of the kind conventionally used in the pharmaceutical art.

Examples of such compositions include capsules, tablets, syrups, granules, solutions in vegetable oils and suspensions. The compositions may be in the form of dosage units containing from 10 to 500 mg of the compounds of Formula I.

The compositions of the invention may be administered from one to three times per day according to the seriousness of the condition being treated and weight of the patient.

We claim:

1. A compound of the formula

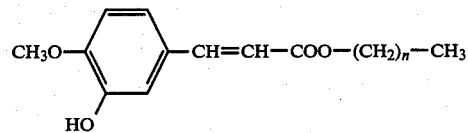

wherein n is from 13 to 25.

2. A compound of the formula

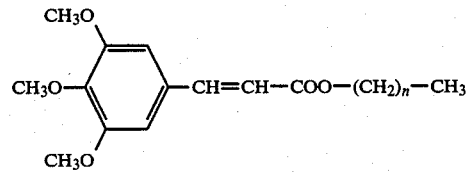

wherein n is from 13 to 25.

3. A method for the treatment of prostatic adenoma, hyperplasia or hypertrophy comprising administering to a patient in need of such treatment an effective amount of a compound of the formula

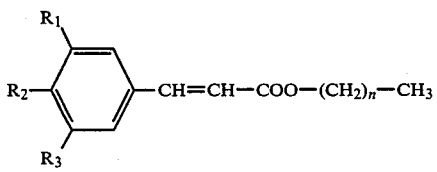

in which $R_1$, $R_2$ and $R_3$, which may be the same or different, are hydrogen, hydroxyl, methoxyl or acetoxyl, and n is from 13 to 25.

4. A method in accordance with claim 3 wherein said compound is selected from the group consisting of docosyl 3-methoxy-4-hydroxycinnamate, docosyl 3-hydroxy-4-methoxycinnimate, docosyl 3,4,5-trimethoxycinnimate, docosyl caffeate, eicosyl 3,4,5-trimethoxycinnimate, tetracosyl 3-methoxy-4-hydroxycinnimate.

5. A method in accordance with claim 3 wherein $R_1$ is hydrogen, $R_2$ is $OCH_3$ and $R_3$ is OH.

6. A method in accordance with claim 3 in which $R_1$, $R_2$ and $R_3$ all represent methoxy.

7. A pharmaceutical composition for use in the treatment or prophylaxis of prostatic adenoma, hypertrophy or hyperplasia and conditions arising therefrom, comprising an effective amount of a compound in accordance with claim 1, together with a pharmaceutically acceptable carrier.

8. A pharmaceutical composition for use in the treatment or prophylaxis of prostatic adenoma, hypertrophy or hyperplasia and conditions arising therefrom, comprising an effective amount of a compound in accordance with claim 2, together with a pharmaceutically acceptable carrier.

9. A pharmaceutical composition, in unit dosage form, for use in the treatment or prophylaxis of prostatic adenoma, hypertrophy or hyperplasia and conditions arising therefrom, comprising a pharmaceutically acceptable carrier and, as active principle, 10–500 mg of a compound of the formula:

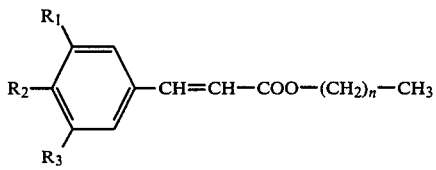

in which $R_1$, $R_2$ and $R_3$, which may be the same or different, are hydrogen, hydroxyl, methoxyl or acetoxyl, and n is from 13 to 25.

10. A pharmaceutical composition, in unit dosage form, for use in the treatment or prophylaxis of prostatic adenoma, hypertrophy or hyperplasia and conditions arising therefrom comprising a pharmaceutically acceptable carrier and, as active principle, a compound of the formula:

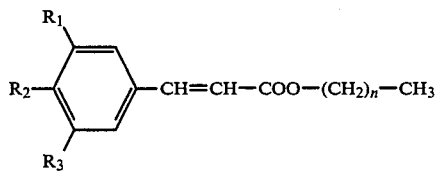

in which $R_1$, $R_2$ and $R_3$, which may be the same or different, are hydrogen, hydroxyl, methoxyl or acetoxyl, and n is from 13 to 25, wherein said composition is in the form of a capsule, tablet, syrup, granules, suspension or a solution in vegetable oil.

11. A composition in accordance with claim 10 wherein said composition is in the form of a capsule or tablet.

12. A composition in accordance with claim 10 wherein said composition is in the form of a solution in vegetable oil.

13. A composition in accordance with claim 10 in unit dosage form.

14. A composition in accordance with claim 13 wherein each said unit dosage contains 10 to 500 mg of said active principle.

* * * * *